United States Patent [19]
Saito et al.

[11] Patent Number: 5,500,355
[45] Date of Patent: Mar. 19, 1996

[54] PROTEASE, REVERSE TRANSCRIPTASE AND ENDONUCLEASE OF HIV-1 AND RSV METHOD FOR PRODUCING THESE ENZYMES

[75] Inventors: Atsushi Saito, Kagawa; Hideo Shinagawa, Osaka; Atsuo Nakata, Toyonaka, all of Japan

[73] Assignee: The Research Foundation for Microbial Diseases of Osaka University, Osaka, Japan

[21] Appl. No.: 82,505

[22] Filed: Jun. 25, 1993

Related U.S. Application Data

[63] Continuation of Ser. No. 443,123, Nov. 30, 1989, abandoned.

[30] Foreign Application Priority Data

Dec. 7, 1988 [JP] Japan .................................. 63-309427
Apr. 6, 1989 [JP] Japan ...................................... 1-88411

[51] Int. Cl.$^6$ .......................... C12P 21/02; C12N 15/48; C12N 15/49; C12N 15/70
[52] U.S. Cl. .................... 435/69.7; 435/69.1; 435/172.3; 435/212; 435/219; 435/320.1; 435/849; 930/221; 935/38; 935/47; 935/73
[58] Field of Search ............................ 435/320.1, 172.3, 435/69.7, 69.1

[56] References Cited

U.S. PATENT DOCUMENTS

| | | | |
|---|---|---|---|
| 4,409,200 | 10/1983 | Feller et al. | 436/516 |
| 4,663,290 | 5/1987 | Weis et al. | 435/252.33 |
| 4,729,955 | 3/1988 | Kodama et al. | 435/183 |
| 4,735,896 | 4/1988 | Wang et al. | 435/5 |
| 4,752,565 | 6/1988 | Folks et al. | 435/5 |
| 5,093,241 | 3/1992 | Bennett et al. | 435/69.4 |

FOREIGN PATENT DOCUMENTS

| | | |
|---|---|---|
| 0215987 | 4/1987 | European Pat. Off. . |
| 0265785 | 5/1988 | European Pat. Off. . |
| 86/06741 | 11/1986 | WIPO . |
| 87/07296 | 12/1987 | WIPO . |

OTHER PUBLICATIONS

S. F. J. LeGrice et al (1987) Gene 55: 95–103.
C. Debouck et al (1987) Proc. Natl. Acad. Sci, USA 84: 8903–8906.
DeLorbe et al., "Journal of Virology", 36(1), 50–61 (1980).
Ruther et al., "The EMBO Journal", 2(10), 1791–1794 (1983).
Adachi et al., "Journal of Virology", 59(2), 284–291 (1986).
Lightfoote et al., "Journal of Virology", 60(2), 771–775 (1986).
Farmerie et al., "Science", 236, 305–308 (1987).
Graves et al., "Proc. Nat'l Acad. Sci. U.S.A.", 85, 2449–2453 (1988).
Schneider et al., "Cell", 54, 363–368 (1988).
LeGrice et al., "The EMBO Journal", 7(8), 2547–2553 (1988).

Primary Examiner—Jacqueline M. Stone
Assistant Examiner—Johnny F. Railey, II
Attorney, Agent, or Firm—Wenderoth, Lind & Ponack

[57] ABSTRACT

Disclosed is a method for producing retroviral proteins which are protease, reverse transcriptase and endonuclease. The method is characterized by the consecutive expression and processing of retroviral genes by the stepwise cultivation of hosts transformed with a vector constructed to carry retroviral gene fragments comprising at least a protease gene and one or more of the other genes coding for retroviral proteins. The retroviral proteins of this invention are used as specific reagents for the diagnosis of retroviral disease, e.g., AIDS, malignant tumors and so forth, also may be used as the basis for research and development of antiviral agents and a vaccine against the above infectious diseases, and for genetic engineering.

2 Claims, 2 Drawing Sheets

Reverse transcriptase activity of crude extraction liquid

Detection of reverse transcriptase and integrase by the Western blot technique

Eluation pattern of reverse transcriptase based on MonQ column chromatography

Fractionation of reverse transcriptase based on Affi-Gel Heparin chromatography

PROTEASE, REVERSE TRANSCRIPTASE AND ENDONUCLEASE OF HIV-1 AND RSV METHOD FOR PRODUCING THESE ENZYMES

This application is a continuation of now abandoned application, Ser. No. 07/443,123, filed Nov. 30, 1989.

FIELD OF THE INVENTION

The present invention relates to enzymes coded by retroviral genes, in particular to protease, reverse transcriptase and endonuclease (integrase) enzymes, and to a method for producing them. More particularly, the present invention relates to a method for producing the above-mentioned enzymes in the form of matured or active individual protein molecules rather than as part of a fused protein molecule, by causing expression of at least one kind of gene in which a protease gene is necessarily selected from the above-mentioned three kinds of enzyme gene groups of retrovirus, namely, the following four sets; the protease gene alone: the protease and reverse transcriptase genes: the protease and endonuclease genes: the protease, reverse transcriptase and endonuclease genes; by means of the recombinant DNA technique, and at the same time, causing procession of the thus expressed product itself by means of protease within the expressed product. In addition, the present invention also relates to various proteins obtained by this method. The present invention provides such enzymes as protease, reverse transcriptase and endonuclease useful for preparing materials for genetic engineering or retrovirus research, materials for developing pharmacotherapy drugs relating to retrovirus infections diseases, diagnostic antigens and diagnostic antibodies, as well as for preparing antigens for vaccines.

PRIOR ART

[Definition of Retrovirus]

A retrovirus is the generic name for viruses classified as belonging to the retrovirus family, and the features common to these viruses are that they have an envelope, single-stranded RNA genome and reverse transcriptase. These viruses include the spherical shape having a diameter of about 80 to 100 nm, composition of two or three molecules of linear (+) stranded RNA genome with molecular weight of about $3 \times 10^6$ in the viral particle. More particularly, the retrovirus family is further classified into the following three subfamilies, i.e., oncovirus, lentivirus and spumavirus (R. E. F. Matthews Edt. "Classification and Nomenclature of Viruses-Fourth Report of the International Committee on Taxonomy of Viruses", pp. 124–128, S. Karger [Switzerland], 1982). Known viruses classified as oncoviruses, also named RNA tumor viruses, include human T cell leukemia virus, feline leukemia virus, murine sarcoma virus, moloney murine leukemia virus, bovine leukemia virus, hog leukemia virus, avian leukemia virus, avian sarcoma virus, arian myeloblastosis virus, and Rous associated virus. Known viruses classified as lentiviruses which are commonly known as viruses causing slow viral infection, include human immunodeficiency viruses types 1 and 2 (hereinafter respectively referred to as "HIV-1" and "HIV-2"), simian immunodeficiency virus, visna virus causing ovine encephalomyelitis, maedi virus causing jaagsiekte, caprine arthritic encephalitis virus, equine infectious anemia virus, and bovine lymphadenitis virus ("Current Topics in AIDS", vol. 1, pp. 95–117, John Wiley & Sons, 1987; Advances in Virus Research, vol. 34, p. 189–215, 1988). The viruses classified as spumaviruses, also named foamy viruses, infect such mammals as humans, monkeys, cattle and cats. Foamy virus and syncytial virus isolated from these hosts are well known. The term retrovirus as used herein can be taken to include all viruses, known as well as unknown, retroviruses characterized as described above.

[Present Situation Concerning Fundamental Research in Retroviral Genes]

Retroviruses are important not only from the point of view of the serious and often lethal infectious diseases which they cause in men and other animals, as well as a contagious disease common to them, but they are also useful for understanding diseases such as sarcoma and for the preparation of material for use in research and genetic engineering. Consequently, as massive reports about these viruses have been made, the present situation concerning typical retroviruses is expediently explained as follows. As is well known, before 1980 retroviruses had been studied, as a material for the oncogenic mechanism, and from the point of view of clarifying strange, slow virus infectious disease which resulted in incurable diseases. Since the discovery of AIDS in the United States in 1981, comparative studies on various retroviruses have intensively been carried out using the full range of techniques in epidemiology, immunology, virology and molecular biology as research materials or experimental models with a view to establishing methods for treatment and prevention of AIDS. A huge volume of useful reports concerning AIDS has already been accumulated (Advances in Virus Research, vol. 34, pp. 189–215, 1988; Annual Review of Immunology, vol. 6, pp. 139–159, 1988; Microbial Pathogenesis, vol. 5, pp. 149–157, 1988). From among these research reports, an outline regarding HIV genes is described below ("HIV and Other Highly Pathogenic Viruses", pp. 33–41, Academic Press, Inc., 1988; "The Control of Human Retrovirus Gene Expression", pp. 79–89, Cold Spring Harbor Laboratory, 1988; Cytological Engineering, vol. 7 (Suppl. 1), pp. S5–S15, 1988): the viral genome forms a complex with a reverse transcriptase and the structural protein in the core of the viral particle, and is present, together with a primer tRNA, in the vital particle; the viral genome comprises about nine different genes, including the basic three major genes encoding the vital particle components essential for virus multiplication, i.e., the gag (group-specific antigen) gene encoding the precursor of the core protein, the pol (polymerase) gene encoding the precursor of three different enzymes, and the env (envelope) gene encoding the precursor of the glycoprotein of the envelope; these genes are arranged from the 5' end to the 3' end in this sequence gag, pol, and env; more specifically, gag. pol. vif . . . and env are arranged adjacent to the respective next ones in this order, and part of the 5' end region of the pol gene overlaps about 240 bases with the 3' end region of the gag gene, with a different reading frame. The frame shifting is thought to occur during translation of this overlapping portion, so that translation proceeds through conversion of the termination codon; expression of the entire region of the pol. gene having a total length of about 3 kb including that overlapping portion leads to production of the above-mentioned enzyme precursor (molecular weight: 160 kd) in the form of a fusion protein $NH_2$—Gag—protease—reverse transcriptase—integrase—COOH, and then, the thus produced polyprotein is cleaved by an existing protease derived from the virus or by the protease activity within the same molecule, and is processed into the individual mature proteins, i.e., into the Gag proteins and the enzymes protease, reverse transcriptase (p66 and p51) and integrase (p32).

All enzymes mentioned above play important roles in the process of multiplication and maturity of virus or in that of provirus formation, and the following functions have been confirmed or presumed: protease participates in post-translational processing, and core formation or maturity process of viral particle, and the action of protease is highly specific toward viruses from which it is derived. Reverse transcriptase functions as an RNA dependent DNA polymerase catalyzing the process of reverse transcription of the genomic RNA into DNA, which is the basic stage of the virus multiplication process, and at the same time, the reverse transcriptase is furthermore known to have the ribonuclease H activity specifically digesting the RNA strand of the RNA-DNA heteroduplex as well as the DNA dependent DNA polymerase activity producing double-stranded DNA, and is popularly used as a tool in genetic recombination. Integrase is an endonuclease acting on the DNA chain, catalyzing recognition and excision of the part to be integrated into the host chromosome which is of linear or circular virus double-stranded DNA reverse—transcribed from viral genomic RNA through the above-mentioned reverse transcription process and is thus considered to participate in the process of formation of provirus.

[Present Situation Concerning Applied Research on Retroviral Gene and Problems Involved]

In the area of applied retroviral gene research, active efforts are being made to express the HIV env gene, principally in an attempt to develop a diagnostic reagent or vaccine against AIDS ("Vaccine", pp. 558–567, W. B. Saunders Company, 1988; Science, vol. 18 [No. 12], pp. 110–119, 1988). With regard to research and development in the application area of retroviral gag and pol genes, the following efforts are known: for example, a suggestion that the protease gene product is useful as a reagent for the development of an anti-retroviral drug having a high specificity as a therapeutic drug and for the fundamental research on retroviruses (Cytological Engineering, vol. 7 [Suppl. 1], pp. S67–S77, 1988); a method for producing reverse transcriptase using a cell strain established from the hog spleen infected with hog leukemia virus falling under the category of oncovirus (Japanese Patent Provisional Publication No. 59-118,081); a method for producing reverse transcriptase using an *Escherichia coli* strain transformed with an expression vector carrying the reverse transcriptase gene of avian sarcoma virus falling under the category of oncoviruses (U.S. Pat. No. 4,663,290); and a method for producing reverse transcriptase comprising preparing a DNA fragment of the reverse transcriptase gene region from pol gene of moloney murine leukemia virus falling under the category of oncoviruses, constructing an expression vector carrying said DNA fragment, and then, purifying the product from the culture of the transformant obtained by introducing said expression vector into *Escherichia coli* (WO 86/06741). Furthermore, the reverse transcriptase enzyme has been used as an antigen in the preparation of a monoclonal antibody for use in the detection of reverse transcriptase derived from avian sarcoma virus (Japanese Patent Provisional Publication No. 61-104,799); as well known currently available, the reverse transcriptase for synthesizing complementary DNA is prepared from avian myeloblastosis virus, and also obtained from moloney murine leukemia virus or Rous associated virus (RAV-2), thus being prepared mainly from the oncovirus itself. As is clear from the above description, the prior art concentrated on the expression of the HIV env gene, components of oncovirus, their oncogenic effect and the use of reverse transcriptase gene thereof. As a matter of practical application, difficulties associated with these prior art techniques include the need to protect against biohazards during manufacturing processes, production cost, production yield, and difficulties relating to enzyme activity, substrate specificity, purity, homogeneity and stability. There is, therefore, a need for the development of a safe low-cost mass production system for high-quality products. At the present time, those relating to the usefulness and industrial application of the various retroviral enzymes do not tend to attract much attention, particularly of researchers. Under these circumstances therefore, the provision of a new method for the mass production of retroviral enzyme products, i.e., protease, reverse transcriptase and integrase at low cost could be expected to stimulate progress in fundamental research relating to viral infection, and the development of pharmacotherapeutic, diagnostic and preventive drugs, and would thus be of considerable significance.

OBJECT OF THE INVENTION

In attempts to overcome the above-mentioned difficulties, we have studied energetically, and as a result achieved a method for mass-producing retroviral enzyme products i.e., enzymes such as protease, reverse transcriptase and integrase, safely in terms of biohazard, at a stable and high production yield, with a low cost.

This achievement is due to success in linking a cDNA fragment prepared so as to necessarily contain a retroviral protease gene with an inducible promotor gene having a high expression ability in a correct reading frame by utilization of the recombinant DNA technology, raising expression of the enzyme gene products, and processing the gene product itself by the expressed protease. We found it possible to produce stably in large quantities the above-mentioned enzymes coded by that cDNA, not as a fusion protein, but individual mature proteins having a specific activity in the culture, by preparing a transformant obtained through introduction of an expression vector carrying the above-mentioned gene cDNA, and applying the two-stage culturing method described later for culture of the said transformant. We found also that such processing was due to the specific activity of protease accounting for part of the fusion proteins which are expression products of the above-mentioned gene, more particularly, that the processing was a phenomenon unique to the retroviral protease. In addition, we have found that these enzymes have very high purity and homogeneity as a result of improved mass production and purification processes, and particularly when retroviral genes expressed resulting enzymes have an activity with a very high substrate specificity unique to retroviruses. The present invention was achieved on the basis of these findings.

According to the present invention, there are provided: a method for producing retroviral enzymes such as protease, reverse transcriptase and integrase; the above-mentioned enzymes as tools in genetic engineering useful for the dissociation and cleavage of viral components, synthesis of complementary DNA, preparation of proviruses through integration of viral genomes into the host cell and transformation of the host cell; the above-mentioned enzymes as tools in protein engineering useful for the functional and structural analysis of protein; the above-mentioned enzymes as virological tools for fundamental and clinical studies useful for the clarification of multiplication mechanism of viruses and for the development of antiviral drugs exerting specific effects on retroviruses; the above-mentioned enzymes useful as diagnostic antigens and for the preparation of diagnostic antibodies to detect retroviral infections, or as antigens for the preparation of immunoglobulin for use in therapy or for the preparation of vaccine for the prevention of secondary infection by retroviruses; and in addition, the above-mentioned enzymes as materials using functions and features of protease, reverse transcriptase and integrase known at present and to be clarified in the future.

DETAILED DESCRIPTION OF THE INVENTION

Figure 1:
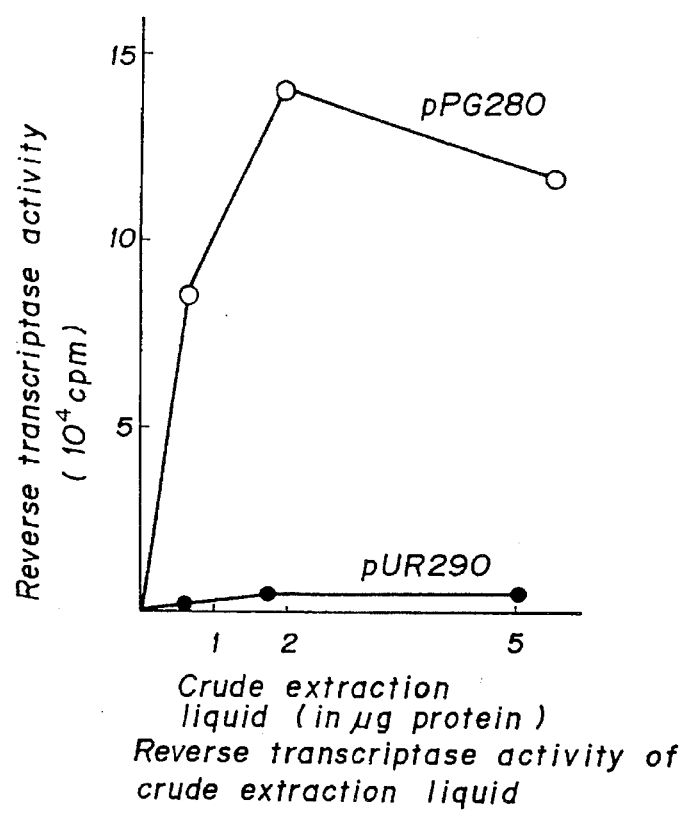
FIG. 1 is a graph illustrating titers of reverse transcriptase activity of the crude extracts of *Escherichia coli* transformed with the plasmid pPG280 carrying the HIV pol gene, and *Escherichia coli* transformed with the vector pUR290 not having the HIV pol gene.

The present invention has the following construction:

(I) Selection of retroviral enzyme genes and preparation of DNA fragments:

Various enzymes of retroviruses founded on the above-mentioned "Definition", such as protease, reverse transcriptase and integrase, can be used in terms of the enzyme gene of a retrovirus. These genes are used from four sets necessarily containing a protease gene, as described in "FIELD OF THE INVENTION". And, in the case of gene expression by means of the recombinant DNA technique, the above-mentioned various genes are used by being converted into a complementary DNA, for the retroviral genome is an RNA. Such cDNA can be prepared by cloning a proviral genome or the integrated genomic DNA. Further, by using a genomic RNA extracted from the vital particle, that cDNA also can be prepared by being selected from the cDNA library which has been made in accordance with conventional method. However, these preparations are not necessarily easy from the viewpoint of avoiding infection by direct operation with a retrovirus having a high degree of hazard. Therefore, in order to avoid biohazards due to such virus and to save labor in the above-mentioned preparation processes, it is recommended to use a known and cloned retroviral genome. As is seen in the general description cited above, the cloning of various retroviral genomes, the preparation of restriction enzyme maps and the determination of nucleotide sequences have already been reported by researchers throughout the world, and utilization of their achievement may be desirable because of their security and convenience. The available clones include, for example, a plasmid SRA2 (Journal of Virology, vol. 36, pp. 50–61, 1980) which carries the avian sarcoma virus genome deposited as BP-3921 at Fermentation Research Institute, Agency of Industrial Science and Technology, 1-3, Higashi 1-chome, Tsukuba-shi, Ibaraki-ken 305, Japan, HIV-1 provirus genome clones, i.e., plasmids pNL3-1, pNL3-2 and pNL4-3 (Journal of Virology, vol. 59[No. 3], pp. 284–291, 1986), and plasmid pNLH402 of *E. coli* strains UT481/ pNLH402 (Microbiology Research Inst. Registration No. 10436) deposited as BP-2417 at the Fermentation Research Institute. cDNA fragments can be prepared from these plasmids by conventional methods, for example, by excising the DNA from the required region of the above-mentioned plasmid clones by means of a restriction enzyme and purifying the resultant product through phenol extraction, chloroform treatment or ethanol precipitation. The restriction enzyme used for excision of the DNA fragments may appropriately be selected by reference to the genomic DNA clone restriction enzyme map. Thus, for example, to excise DNA fragments from the entire gene region of the above-mentioned pNLH402, the restriction enzyme HindIII (Journal of Virology, vol. 59, pp. 284–291, 1986) may be employed.

(II) Production of an expression vector, and preparation of a transformant containing the vector:

An expression vector is produced by linkage with the retroviral genomic cDNA fragment prepared as described above by a conventional method such as that using T4DNA ligase. Any of the following vectors may be used for expression purposes; those conventionally known or commercially available, for example, plasmid vectors of the pSN508 series of the enteric bacteria family (U.S. Pat. No. 4,703,005), plasmid vector pJM105 (Japanese Patent Provisional Publication No. 62-286,930), vectors of pBH103 series (Japanese Patent Provisional Publication No. 63-22, 098) of yeast, attenuated varicella virus vector (Japanese Patent Provisional Publication No. 53-41,202), attenuated Marek's disease virus vector (Journal of the Japan Veterinary Society, vol. 27, pp. 20–24, 1984; and Gan Monograph on Cancer Research, vol. 10, 1971), Escherichia coli plasmid vector pUR290 series (EMBO Journal, vol. 2 [No. 10], pp. 1791–1794, 1983), and pSN5182 (Journal of Bacteriology, vol. 157, pp. 909–917, 1984). What is important in the production of the expression vector is to link the above-mentioned enzyme gene in a matching reading frame with a gene which is capable of being highly expressed. Thus for example, when using pUR290 referred to above, the pol gene should preferably be inserted downstream of lacZ gene of the plasmid, or in the case of pSN5182, downstream of the plasmid pstS gene. Furthermore, for carrying that gene, attention should be given to matching the codon reading frames among the genes so as to ensure smooth progress of translation. For example, when the cDNA of viruses such as HIV-1, HIV-2, simian immunodeficiency virus and moloney murine leukemia virus are inserted, the reading frame of the pol gene is linked so as to match with those of genes with high expressing ability, because the protease of such viruses as described above are encoded in the pol gene region. On the other hand, a protease of avian sarcoma virus is encoded in the gag gene region having a different reading frame from the pol gene, and the protease gene of human T-cell leukemia virus or bovine leukemia virus has yet another reading frame differing from those of both the pol and gag genes. In these cases, care is needed to match the reading frames of all the genes, i.e., the retroviral genes e.g. protease gene, pol gene and the gene with high expressing ability, in order to ensure significant expression of the retroviral genes. Matching of the reading frames above can be accomplished using conventional techniques employing enzymes such as restriction enzyme, nuclease Ba131 and mung bean nuclease. The optimum recipient cell used for the purpose of obtaining a transformant through introducing of the thus constructed expression vector should be selected from among host cells allowing multiplication and expression of that expression vector, and at the same time, from these host cells, a cell permitting easy introduction of the expression vector constructed as mentioned above and the detection method should be carefully selected and used. When using the above-mentioned pSN series plasmids as the expression vector for example, it is desirable to use *Escherichia coli* C75 strains (Microbiology Research Inst. Registration No. 10191) as the host cells, which are transformed in appearance from an alkaline phosphatase non-productive bacteria into a productive one by the introduction of that vector, as the recipient bacteria, and when using pUR290 series, it is able to employ *Escherichia coli* UT431 (Journal of Bacteriology, vol. 163, pp. 376–384, 1985) which permits selection of a transformant introduced with this vector, with ampicillin resistance as the marker. Introduction of the expression vector into such a recipient cell may be accomplished by a conventional method such as the calcium chloride method (Journal of Molecular Biology, vol. 53, pp. 154–162, 1970). The transformant introducing the enzyme gene expression vector as described above is selected by the above-mentioned marker from the positive colony. Then, after extracting the expression vector DNA through selection from the colony of transformant, it is digested with a restriction enzyme, and the resultant DNA fragments are subjected to agarose gel electrophoresis. Subsequently, the size of the inserted DNA fragment can be measured, and simultaneously, the colony in which the presence of DNA fragment of that gene has been confirmed is adopted as the transformant clone of retroviral enzyme gene expression. For example, when insertion covers the entire pol gene region prepared from pNLH402 into the above-mentioned expression vector pUR290, EcoRI fragment of about 4 kb DNA can be detected.

(III) Confirmation of retroviral enzyme genes expression by the transformant clone and mass production of various enzymes by culture of said transformant:

Confirmation of the enzyme gene expression by the transformant clones can be accomplished, for example, by analyzing the crude extraction liquid of the products of that clone by the use of the Western blot technique. The crude extract can be prepared, for example, by culturing and inducing the transformant in a conventional culture medium, collecting cells by low-speed centrifugation, treating the collected cells with sodium dodecyl sulfate and 2-mercaptoethanol, subjecting them to high-speed centrifugation, and collecting the supernatant liquid. The Western blot technique may be carried out in accordance with the conventional procedure using various commercially available materials in the following steps: subjecting the above-mentioned crude extracts to polyacrylamide gel electrophoresis; transferring the separated protein onto a nitrocellulose membrane by use of a transblotting apparatus, and immersing the membrane into gelatin solution for blocking. The subsequent steps include, when the specimen on the membrane is an HIV pol gene product, for example: causing a primary reaction with human serum of HIV carrier; causing a secondary reaction with peroxidase-conjugated anti-human IgG antibody after washing; causing coloring with hydrogen peroxide solution and a chromogenic agent after washing and detecting a band specifically reacting with the human serum of HIV carrier, thereby confirming expression of the pol gene by the above-mentioned clone. In the case of the specimen being the gene product originating from a retrovirus other than HIV, human serum of an HIV carrier is not employed, but an appropriate retroviral antiserum is used for the primary reaction, and an antibody to human or animal IgG is used for the secondary reaction.

Mass production of the various enzymes such as protease, reverse transcriptase and integrase through culture of transformant for which enzyme expression has been confirmed is conducted as follows: the transformant of *Escherichia coli* is cultured in LB medium at a temperature of from 30° to 40° C. for from 12 to 35 hours until a bacteria concentration of from 109 to $10^{10}$ cells/ml is reached to prepare seeds for large-scale culture of that transformant; then, inoculating such seeds into fresh medium prepared, and conducting two-stage culture consisting of a pre-culture and an after-culture. The pre-culture is carried out for the purpose of multiplying seed cells and amplifying the expression vector at a temperature of from 10° to 40° C. for from 1 to 24 hours, or more preferably at a temperature of from 15° to 37° C. for from 2 to 12 hours. The pre-culture is discontinued, in the case of *Escherichia coli*, with a concentration of bacteria in culture, i.e., a turbidity of the culture liquid of $OD600_{nm}=0.4$ to 0.7 as the standard. Subsequently, upon completion of this pre-culture, conditions for the induction-culture should be carefully set so that transcription and translation of the enzyme gene linked to the expression vector and the gene product after translation are properly modified, and to achieve individual and single matured proteins having activity, as well as to avoid having the enzyme gene product after translation being decomposed in an unorderly manner by proteolytic enzyme originating from the host cells thus losing its activity. The culture induced should preferably be carried out at a temperature of from 10° to 30° C. for from 1 to 40 hours, or more preferably, at a temperature of from 15° to 28° C. for from 3 to 35 hours. Considering the property of the expression vector used, expression may be induced or accelerated, for example, by causing starvation of phosphate ion in the medium at the start of the induction-culture or by adding and mixing an inducer into the medium. Application of the abovementioned two-stage culture permits production of various enzymes of retroviruses such as protease, reverse transcriptase and integrase, not in the form of fusion proteins, but as independent active proteins, i.e., as individual and single mature proteins usually at a high yield of from 1 to 10 mg per liter of medium.

(IV) Purification of various retroviral enzymes such as protease, reverse transcriptase and integrase which are mass produced by means of an expression vector:

This step can be accomplished by any combination of conventional methods, including, for example, extraction of the cultured product of the transformant through the use of precipitants, centrifugation or filtration; preparation of crude extracts through breakage or crushing of the transformed cells by the application of ultrasonic treatment, high pressure treatment or a homogenizer; purification through adsorption-elution treatment by means of silica or activated charcoal, salting-out, or precipitation by means of organic solvents; high-grade purification by means of ultracentrifugation, column chromatography or electrophoresis; or a method for purifying a gene product through fractionation by density-gradient centrifugation following adsorption-elution with silica and activated charcoal (Japanese Patent Provisional Publication No. 63-297).

The enzymes such as protease, reverse transcriptase and integrase available by the method of the present invention may be provided in the form of liquid, dried powder or adsorbed onto filter paper or a membrane, and enclosed in an ampule, a vial or other small container. In the dried powder, the enzyme may be used in a necessary amount after dissolving in distilled water to the volume before using. When it is adsorbed onto filter paper or membrane, it should be used after wetting with a solution as prescribed in the instructions.

The method of the present invention is described below in more detail with reference to examples. The present invention is not limited to the examples described below.

(Experiment 1)

Measurement of activity of reverse transcriptase: a reaction mixture is made up comprising 50 mM tris-HCl(pH 8.3), 50 mM potassium chloride, 10 mM magnesium chloride, 3 mM dithiothreitol, 0.1 W/V% Nonidet P-40 (made by Shell Oil [U.S.A.]), 20 µg/ml $(rA)_n(dT)_{12-18}$ (Pharmacia [Sweden]), 0.5 mM dTTP (deoxy thymidine triphosphate), and 1 µCi [$^3$H] dTTP (deoxy thymidine triphosphate). To this reaction mixture was added specimen in an amount of 5 µl into a total volume of 50 µ, and the mixture was incubated at 37° C. for 10 minutes. Then the mixture is immediately cooled on ice, and filtered through a filter paper DE81 (made by Wattman [England]). The filter is washed well with 5% sodium phosphate solution, and then with ethanol after water rinsing. After drying, radioactivity is measured by means of a liquid scintillation counter.

(EXAMPLE 1)

Construction of an expression vector carrying the pol gene of lentivirus: 5 µg of plasmid pNL4-3 DNA (Journal of Virology, 59(2): 284–291, 1986) carrying the HIV proviral genome DNA was added to 5 µl HindIII, 20 µl 5×RM (50 mM tris-HCl [pH 7.5], 35 mM $MgCl_2$, 300 mM NaCl), diluted with distilled water to a total volume of 100 µl, and after incubation at 37° C. for an hour, extraction of the solution was carried out with phenol saturated with TE(10 mM tris-HCl [pH 7.5], 1 mM EDTA). The water layer was treated with chloroform before ethanol precipitation. To the mixture of 1 µl of the solution prepared by dissolving the precipitation into 10 µl TE, 0.1 µg (1 µl) of plasmid pHSG398 DNA cleaved by HindIII and treated with alkaline phosphatase, and 2 µl of 10×ligation buffer (660 mM tris-HCl [pH 7.6], 66 mM $MgCl_2$, 100 mM DTT and 1 mM ATP), 1 µl T4DNA ligase was further added and the total volume was brought up to 20 µl with distilled water. Then, incubation was applied at 15° C. for 12 hours. Subsequently, *Escherichia coli* strain JM103 was transformed with this reaction liquid in accordance with the calcium chloride method (Journal of Molecular Biology), 53: 154, 1970), and chloramphenicol resistant colonies were selected on an LB medium plate (1 W/V% Bactotrypton, 0.5 W/V% Bacto-yeast extract, 1 W/V% NaCl and 1.5 W/V% agar) containing 20 µg/ml choramphenicol. Plasmid DNA was extracted from the chloramphenicol resistant clone by a conventional method, and clone pNLH402 was obtained by selecting a clone containing about 4.0 kb fragments originating from plasmid pNL4-3 DNA through HindIII excision.

HindIII in an amount of 5 µl and 5×RM in an amount of 10 µl were added to 5 µl (5 µg) of plasmid pNLH402 DNA, and the mixture was diluted with distilled water to a total volume of 50 µl. The mixture was incubated at 37° C. for an hour, and after phenol extraction and chloroform treatment, the mixture was subjected to ethanol precipitation. The resulting precipitate was added to 10 µl of 5×RM and 5 µl of BglII and was diluted with distilled water to a total volume of 50 µl, whereby it was completely dissolved. The mixture was incubated again at 37° C. for an hour, and after phenol extraction and chloroform treatment, the resulting product was subjected to ethanol precipitation. The thus obtained DNA was dissolved into 10 µl of TE.

At the same time, 5 µl of HindIII and 10 µl of 5'RM were added to 5 µg of expression vector pUR280 DNA (The EMBO Journal, 2(2):1791–1794, 1983). The mixture, diluted with distilled water to 50 µl, was incubated at 37° C. for an hour, and after phenol extraction, chloroform treatment and ethanol precipitation, 10 µl of 5×RM (NaCl concentration: 500 mM) and 5 µl of BamHI were added to it. 35 µl of distilled water were further added so as to cause complete dissolution of the precipitate, and the solution was then incubated at 37° C. for an hour. After phenol extraction and chloroform treatment, DNA precipitated with ethanol was dissolved into 10 µl of TE.

Then, pUR290 DNA (1 µl) digested with HindIII and BamHI was mixed with pNLH402 DNA (1 µl) digested with HindIII and BglII and 2 µl of 10×ligation buffer and 1 µl of T4DNA ligase were added. A total volume of 20 µl was achieved with distilled water, and reaction was caused at 15° C. for 12 hours. *Escherichia coli* strain UT481 (Journal of Bacteriology, 163: 376–387, 1985) was transformed with the reaction liquid in accordance with the above-mentioned calcium chloride method. Ampicillin resistant colonies were selected on an LB medium plate containing 20 µg/ml ampicillin, and furthermore, a clone containing fragments of about 3.8 kb originating from pNL4-3 was selected by measuring the size of the inserted fragment by EcoRI cleavage. Clone UT481/pPG280 was thus obtained. More specifically, in this clone the approximately 3.8 kb HIV pol gene region is considered to be ligated to the 3' end of lacZ gene of plasmid pUR290, and the lacZ and pol gene product is initially expressed as a fusion protein (about 230 kd), the various separate enzymes being produced after processing.

(EXAMPLE 2)

Figure 2:
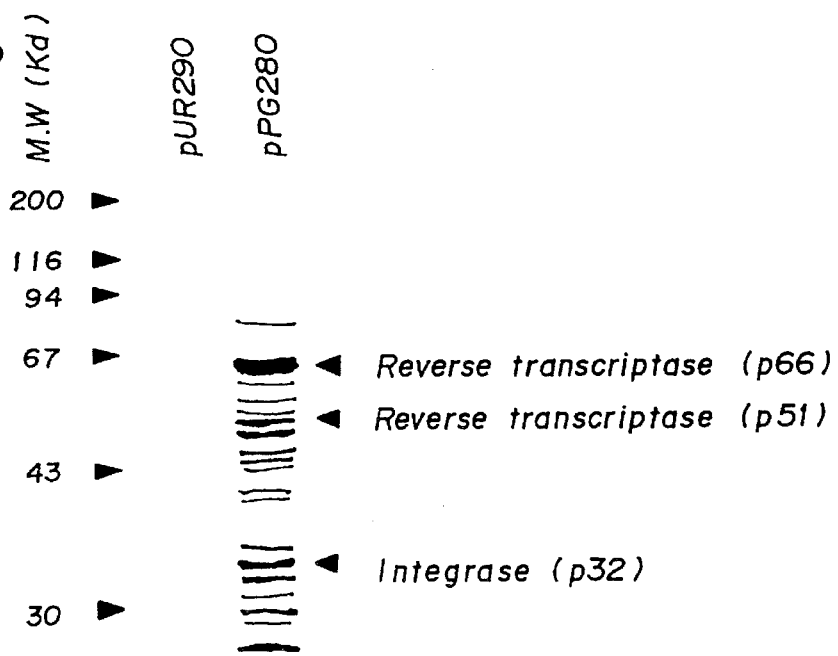
FIG. 2 is a graph illustrating the result of Western blot analysis using human serum obtained from HIV carriers, of crude extracts of *Escherichia coli* transformed with the plasmid pPG280 carrying the HIV pol gene and the vector pUR290 not carrying the HIV pol gene.
Figure 3:
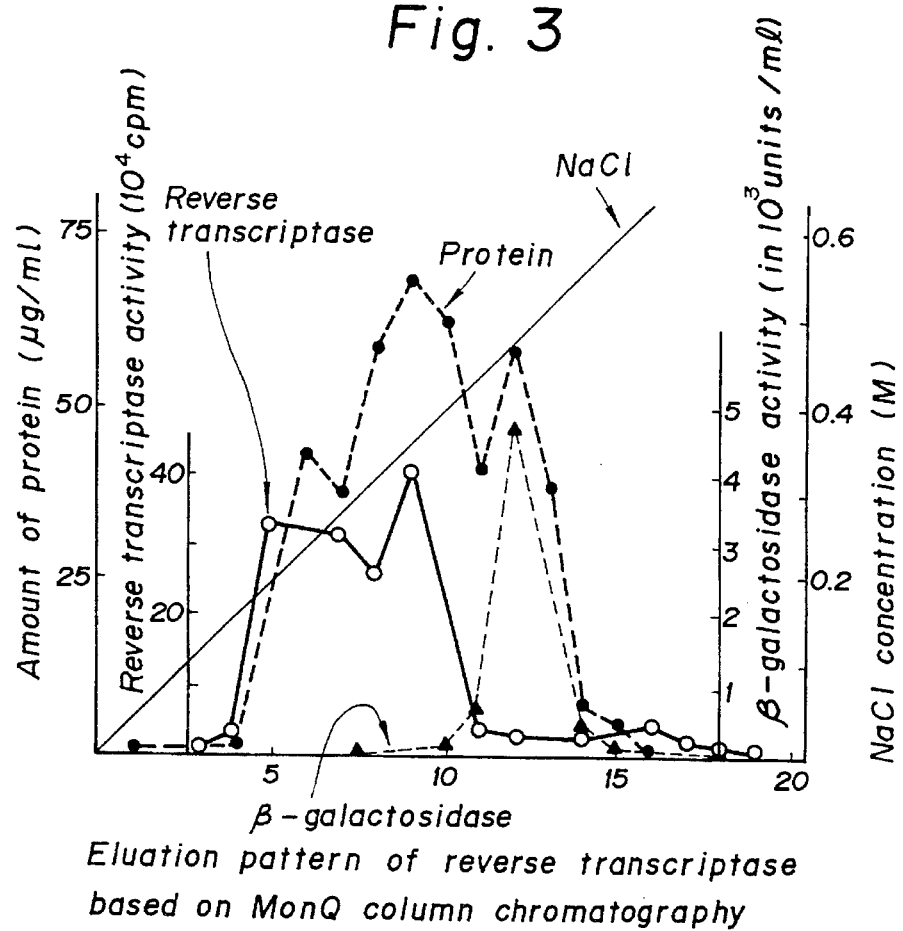
FIG. 3 is a graph illustrating the elution profile of reverse transcriptase derived from *Escherichia coli* crude extracts on an anion exchange column.

Production of lentiviral protease, reverse transcriptase and integrase enzymes by culture of transformed cells: After culturing transformed cell clone UT481/pPG280 at 37° C. for 18 hours in an LB medium containing 20 µg/ml ampicillin (1 W/V% Bactotrypton, 0.5 W/V% Bacto-yeast extract and 1 W/V% NaCl), the resultant cells were added to fresh LB medium containing 20 µg/ml ampicillin at 1:100 dilution and the pre-culture was carried out. When the $OD600_{mm}$ of the medium reached 0.5, 1 mM IPTG (Isopropyl-β-D-thiogalactopyranoside, made by Sigma [U.S.A.]) was added, and culture was continued at 25° C. for 18 hours. Bacteria were collected by centrifugation (5,000 rpm for five minutes) and suspended in 1/25 volume of 40 mM tris-HCl (pH 8.0) (0.1 mM EDTA, 5 mM $MgCl_2$, 0.1 W/V% Triton X-100 and 10 mM 2-mercaptoethanol). After ultrasonic treatment (five 30-second bursts, 19.5 kHz, 300 W), the supernatant liquid was separated by centrifugation (19,000 rpm, 60 minutes). To confirm the presence of HIV pol gene product in this crude extraction liquid, the activity of the reverse transcriptase in the crude extraction liquid was measured. The result is shown in FIG. 1. The expected significant activity of the reverse transcriptase was observed. Analysis by the Western blot technique was also carried out: 4 W/V% sodium dodecyl sulfate (SDS) and 1 W/V% 2-mercaptoethanol were added to the collected bacteria. After boiling for five minutes and centrifugation (10,000 rpm for five minutes), the supernatant liquid was electrophoresed on a 0.1 W/V% SDS—10 W/V% polyacrylamide gel. After blotting onto a nitrocellulose membrane (made by S&S [West Germany]) by means of transblotting apparatus (made by Bio-Rad [U.S.A.]), the membrane was immersed in 3 W/V% gelatin solution in accordance with the conventional blocking method. Then, as a primary reaction the membrane was incubated with human serum obtained from an HIV carrier, and after washing, as a secondary reaction was caused with peroxidase marker conjugated anti-human IgG antibody (made by BioRad). Finally, after washing, the membrane was immersed in a chromogenic liquid prepared by adding 0.4 ml of DAB (3,3'-diaminobenzidine tetrahydrochloride) and 15 μl of 30 W/V% hydrogen peroxide solution to 50 ml of TBS (20 mM tris-HCl [pH 7.4], 500 mM NaCl), to cause color formation, at room temperature for 15 minutes, and was then washed with distilled water. The result is shown in FIG. 2. While no specific band reacting with human HIV carrier serum was observed in the crude extraction liquid of the transformed cell UT481/pUR290 based on the vector pUR290 not carrying an HIV pol gene, bands of reverse transcriptase having a molecular weight of 66 kd and 51 kd, integrase of 32 kd, and protease of 12 kd, i.e. the HIV pol gene products, were observed in the extraction liquid of transformed cells of strain UT481/pPG280. Cleavage of the reverse transcriptase from β-galactosidase is easily determined from the results of column chromatography with anion exchanger MonoQ (made by Pharmacia [Sweden]) as shown in FIG. 3. More particularly, the reverse transcriptase activity can be found in a fraction completely separated from β-galactosidase activity. This suggests that, although HIV pol gene products are produced as fusion proteins with β-galactosidase, protease, reverse transcriptase, and integrase regions of that fusion protein are specifically separated by the action of the protease which is itself a pol gene product, and accumulated in the cell.

(EXAMPLE 3)

Construction of a vector to enable the production of large amounts of lentiviral protease: 5 μl of HindIII and 10 μl of 5×RM were added to 5 μg of DNA of the pol gene expression plasmid pPG280 prepared in Example 1, and the mixture was diluted with distilled water to a total volume of 100 μl. The mixture was incubated at 37° C. for an hour, and after phenol extraction and chloroform treatment, the mixture was subjected to ethanol precipitation. The resultant precipitation was added to 5 μl of 5×RM (–NaCl) and 5 μl of BalI and was diluted with distilled water to a total volume of 50 μl, whereby the precipitate was sufficiently dissolved. The mixture was incubated again at 37° C. for an hour, and after phenol extraction and chloroform treatment, the resulting product was subjected to ethanol precipitation. The resulting precipitation was added to 5 μl of 10×polymerase buffer (670 mM Tris HCl [pH 8.8], 67 mM $MgCl_2$, 166 mM $(NH_4)_2SO_4$, 100 mM 2-mercaptoethanol and 67 μM EDTA), 5 μl of 10×dNTP solution (each 3.3 mM of dATP, dGTP, dTTP, and dCTP) and 1 μl T4 DNA polymerase and was diluted with distilled water to a total volume of 50 μl, whereby it was sufficiently dissolved. The mixture was incubated at 37° C. for 15 minutes, and after phenol extraction and chloroform treatment, the resulting product was subjected to ethanol precipitation. To the mixture of 1 μl of the solution prepared by dissolving the resultant precipitation into 10 μl of TE and 2 μl of 10×ligation buffer, 1 μl of T4 DNA ligase was further added and total volume was brought up to 20 μl with distilled water. The mixture was further incubated at 15° C. for 12 hours. Escherichia coli strain UT481 was transformed with this reaction liquid in accordance with the above-mentioned calcium chloride method. Ampicillin resistant colonies were selected on an LB medium plate containing 20 μg/ml ampicillin, and furthermore, a clone containing 0.55 kb fragment originating from pNL4-3 was selected by measuring the size of the inserted fragment using EcoRI digestion. Clone UT481/pLB550-3 was thus obtained.

(EXAMPLE 4)

Mass production of lentiviral protease by transformed cells: After culturing transformant clone UT481/pLB550-3 at 37° C. for 18 hours in LB medium (containing 20 μg/ml ampicillin), the resulting cells were added to fresh LB medium (containing 20 μg/ml ampicillin) at 1:100 dilution and the pre-culture was carried out at 37° C. When the $OD600_{nm}$ of the medium reached 0.5, 1 mM IPTG (Isopropyl β-D-thiogalactopyranoside, Sigma [U.S.A.]) was added, and culture was continued at 37° C. for 6 hours. Bacteria were collected by centrifugation (5,000 rpm for five minutes), and 4 W/V% sodium dodecyl sulfate (SDS) and 1 W/V% 2-mercaptoethanol were added. After boiling for five minutes and centrifugation (10,000 rpm for five minutes), the supernatant liquid was electrophoresed on a 0.1 W/V% SDS—15 W/V% polyacrylamide gel. Subsequently, the collected bacteria were analyzed by means of the Western blot technique described in Example 2. While no specific band reacting with human HIV carrier was observed in the crude extracts of UT481/pUR290, bands of 12 kb protease serum were observed in the extracts liquid of UT481/pLB550-3. Especially, pLB550-3 produced an amount of protease several times as much as pPG280. In this clone, 0.55 kb HIV pol gene is considered to be ligated to the 3' end of lacZ gene of plasmid pUR290, and the lacZ—pol gene product is estimated to be produced as a fusion protein with molecular weight of about 140 kb, and a protease of about 12 kb being produced after processing.

(EXAMPLE 5)

Construction of an expression vector carrying oncoviral protease and pol gene: 5 μg of plasmid pSRA2 DNA carrying Rous sarcoma virus cDNA (Journal of Virology, 36, pp. 50–61, 1980) was added with 5 μl of BamHI and 20 μl of 5×RM, and was diluted with distilled water to a total volume of 100 μl, which was then incubated at 37° C. for an hour. After this reaction, the mixture was electrophoresed on a 1 W/V% agarose gel having a low melting point, and the gel portion containing a 1.8 kb DNA fragment was digested. Then, after phenol extraction and chloroform treatment, the resulting product was subjected to ethanol precipitation. To the mixture of 1 μl of the solution prepared by dissolving the precipitation into 10 μl of TE, 0.1 μg (1 μl) of plasmid pUR291 DNA cleaved by BamHI and treated with alkaline phosphatase, and 2 μl of 10×ligation buffer, 1 μl of T4 DNA ligase was further added and the total volume was brought up to 20 μl with distilled water. The reaction mixture was incubated at 15° C. for 12 hours. Subsequently, Escherichia coli strain UT481 was transformed with this reaction mixture in accordance with the calcium chloride method, and ampicillin resistant colonies were selected on an LB medium plate containing 20 μg/ml ampicillin. Plasmid DNA was extracted from the ampicillin resistant clone using a conventional method, and a clone pSR281 was obtained by selecting a clone containing a 1.8 kb fragment originating from plasmid pSRA2 and producing a LacZ-Gag fusion protein.

5 μg of plasmid pSRA2 DNA was added to 5 μl of PstI and 20 μl of 5×RM (750 mM NaCl), and was diluted with distilled water to a total volume of 100 μl, which was then incubated at 37° C. for an hour. After this reaction, the mixture was electrophoresed on a 1 W/V% agarose gel having a low melting point, a 1.8 kb DNA fragment was digested. Then, after phenol extraction and chloroform treatment, the resulting product was subjected to ethanol precipitation and dissolved to 10 μl of TE. Similarly, the double-stranded phage DNA of M13mp18 was cleaved by PstI and treated with alkaline phosphatase. A 1 μl (0.1 μg) of this DNA was added to 1 μl of 3.1 kb DNA fragment mentioned above, 2 μl of 10×ligation buffer and 1 μl of T4 DNA ligase, and was diluted with distilled water to total volume of 100 μl, which was then incubated at 15° C. for 12 hours. Subsequently, the recombinant phage DNA was used to transfect *Escherichia coli* strain TG1 following the calcium chloride method, and a plaque was formed on a 2YT medium plate (1.6 W/V% Bacto-trypton, 1 W/V% Bacto-yeast extract, 0.5 W/V% NaCl and 1.5 W/V% Bacto-agar) containing an X-gal (5-brom-4-chloro-3-indolyl-β-D-galactopyranoside, Sigma [U.S.A.]).

Next, the TG1 strain was propagated in a 2YT medium (1.6 W/V% Bacto-trypton, 1 W/V% Bacto-yeast extract, and 0.5 W/V% NaCl) until the OD600$_{nm}$ of the medium reached 0.3, and some of the achromatic clone of the resultant plaque were inoculated. Each single- and double-stranded DNA was prepared in accordance with a conventional method after continuing to incubate for several hours. A clone M13sr31 which contains a 3.1 kb fragment originating from pSRA2 was selected by digesting the obtained double-stranded DNA with PstI and BamHI. The 3.1 kb fragment originating form pSRA2 encodes the 3' end of gag gene, the termination codon TAG, and the pol gene. The insertion of one base before the termination codon results in the expression of a gag-pol fusion gene having matching translating frames. Thus by using an in vitro mutagenesis kit (made by Amersham [England]), a clone M13sr32 was obtained, containing the sequence ATAG obtained by inserting one base before the termination codon TAG on the M13sr31.

5 μg of double-stranded DNA of M13sr32 was added to 5 μl of PstI and 20 μl of 5×RM, and was diluted with distilled water to total volume of 100 μl, which was then incubated at 37° C. for an hour. After this reaction, the mixture was electrophoresed on a 1 W/V% agarose gel having a low melting point, and a gel containing a 3.1 kb DNA fragment was digested. Then, after phenol extraction and chloroform treatment, the resulting product was subjected to ethanol precipitation. To the mixture of 1 μl of the solution prepared by dissolving the precipitation into 10 μl of TE, 1 μl (0.1 μg) of plasmid pSR281 DNA digested by PstI and treated with alkaline phosphatase, and 2 μl of 10×ligation buffer, 1 μl of T4 DNA ligase were further added and the total volume was brought up to 20 μl with distilled water. Then, the mixture was incubated at 15° C. for 12 hours. Subsequently, *Escherichia coli* UT481 strain was transformed with this reaction mixture in accordance with the calcium chloride method, and ampicillin resistant colonies were selected on an LB medium plate containing 20 μg/ml ampicillin. Plasmid DNA was extracted from the ampicillin resistant clone by a conventional method, and the presence and direction of the 3.1 kb fragment originating from M13sr32 were confirmed by digesting the plasmid by PstI and BamHI, and then a clone UT481/pSR271 which was assumed to express protease and pol gene products was obtained.

Incidentally, the thus obtained clone UT481/p5R271 carries a total of 3.6 kb DNA derived from pSRA2, because the 1.3 kb region of pSR281 which overlaps the 31. kb region of M13 sr 32 was removed by Pst I cleavage.

(EXAMPLE 6)

Production of oncoviral protease, reverse transcriptase and integrase enzymes by culture of transformed cells: After culturing transformant clone UT481/pSR271 at 37° C. for 18 hours in an LB medium (containing 20 μg/ml ampicillin), the resultant cells were added to fresh LB medium (containing 20 μg/ml ampicillin) at 1:100 dilution and the pre-culture was carried out. When the OD600$_{nm}$ of the medium reached 0.5, 1 mM IPTG was added, and culture was continued at 25° C. for 18 hours. Bacteria were collected by centrifugation (5,000 rpm for five minutes) and suspended in $\frac{1}{25}$ volume of 40 mM tris-HCl (pH 8.0) (0.1 mM EDTA, 5 mM MgCl$_2$, 0.1 W/V% Triton X-100 and 10 mM 2-mercaptoethanol). After ultrasonic treatment (five 30-second bursts, 19.5 kHz, 300 W), the supernatant was separated by centrifugation (19,000 rpm, 60 minutes). To confirm the presence of RSV gene product in this crude extraction liquid, the activity of the reverse transcriptase in the crude extraction liquid was measured. The expected significant activity of the reverse transcriptase was observed. Analysis by the Western blot technique was also carried out: 4 W/V% sodium dodecyl sulfate (SDS) and 1 W/V% 2-mercaptoethanol were added to the collected bacteria. After boiling for five minutes and centrifugation (10,000 rpm for five minutes), the supernatant was electrophoresed on a 0.1 W/V% SDS—15 W/V% polyacrylamide gel. After blotting onto a nitrocellulose membrane (made by S&S [West Germany]) using transblotting apparatus (made by BioRad [U.S.A.]), the membrane was immersed in 3 W/V% gelatin solution in accordance with the conventional blocking method. Then, as a primary reaction, the membrane was incubated with anti-RSV rabbit serum, and after washing, as a secondary reaction was incubated with peroxidase marker conjugated anti-rabbit IgG antibody (made by BioRad). Finally, after washing, the membrane was immersed in a chromogenic liquid prepared by adding 0.4 ml of DAB (3.3'-diaminobenzidine tetrahydrochloride) and 15 μ of 30 W/V% hydrogen peroxide solution to 50 ml of TBS (20 mM tris-HCl [pH 7.4], 500 mM NaCl), to cause color formation, at room temperature for 15 minutes, and was then washed with distilled water. While no specific band reacting with anti-RSV rabbit serum was observed in the crude extraction liquid of the transformed cell UT481/pUR290 based on the vector pUR290 not having the RSV gene, bands of RSV reverse transcriptase were observed in the extraction liquid of UT481/pSR271. Although RSV protease and the pol gene product are produced as a fusion protein with β-galactosidase, proteases and reverse transcriptase regions are specifically separated by the action of the protease which is itself a gag gene product, and are estimated to be accumulated in the cell. In the clone UT481/pSR271, the 3.6 kb Rous sarcoma virus gag and pol gene region is considered to be ligated to the 3' end of lacZ gene of plasmid pUR291, and it is suggested that the lacZ, gag and pol gene products are expressed as a fusion protein (about 230 kb), which is then processed to liberate the enzymes e.g. protease (P15), reverse transcriptase (P92, P65) and integrase (P32).

(EXAMPLE 7)

Extraction of reverse transcriptase: As mentioned above in Example 2, transformed *Escherichia coli* clone UT481/pPG280 was cultured in 9l LB medium (containing 20 μg/ml ampicillin) at 25° C., and when the culture reached an OD600$_{nm}$ of 0.5, 1 mM IPTG was added. Culture was further continued for another 24 hours, and after collection, the cells were suspended in 120 ml of 40 mM tris-HCl (pH 8.0) (containing 0.1 mM EDTA, 5 mM MgCl$_2$, 0.1 W/V% Triton X-100 and 10 mM 2-mercaptoethanol) buffer. Bacterial cells were crushed by ultrasonic treatment and subjected to centrifugation (19,000 rpm for 60 minutes), and the supernatant was separated as the crude extraction liquid.

(EXAMPLE 8)

Purification of reverse transcriptase: Polymine P (made by BRL [U.S.A.]) was added in an amount of 0.1 W/V% to the crude extraction liquid, which was then stirred at 4° C. for 30 minutes and centrifuged (16,000 rpm for 20 minutes).

Ammonium sulfate was added to the supernatant. The precipitate produced from this 40% saturated solution was removed by centrifugation (16,000 rpm for 20 minutes) and 137 ml of supernatant liquid was obtained. Ammonium sulfate was added again to 80% saturation, and the thus produced precipitate was dissolved in 50 ml of the above-mentioned 40 mM tris-HCl buffer and was then dialyzed against same buffer containing 50 mM NaCl.

(EXAMPLE 9)

Figure 4:
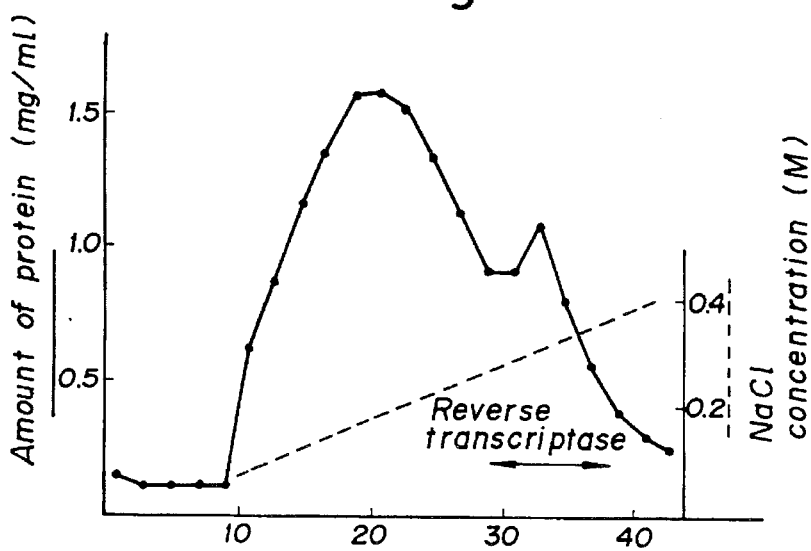
FIG. 4 is a graph illustrating separation of reverse transcriptase by Affi-Gel Heparin chromatography.

High grade purification of reverse transcriptase: High grade purification was carried out using DEAE Bio-Gel A (made by BioRad [U.S.A.]) and Affi-Gel Heparin column chromatography (made by BioRad). The dialyzed sample of Example 8 was applied to a 30 ml DEAE Bio-Gel A column equilibrated with 40 mM tris-HCl (pH 8.0) (containing 0.1 mM EDTA, 5 mM $MgCl_2$, 0.1 W/V% Triton X-100, 10 mM 2-mercaptoethanol and 50 mM NaCl). The eluted sample was then applied to a 30 ml Affi-Gel Heparin column equilibrated with the above-mentioned buffer and was eluted with 150 ml buffer comprising a sodium chloride gradient of from 50 mM to 400 mM. The result is shown in FIG. 4. Fractions 29 to 38 containing reverse transcriptase activity were pooled. The thus pooled reverse transcriptase fractions were dialyzed against 20 mM sodium phosphate buffer (pH 6.8) (containing 0.1 mM EDTA, 5 mM $MgCl_2$, 0.1 W/V% Triton X-100 and 10 mM 2-mercaptoethanol) and were further purified by the use of hydroxylapatite column (KB column, made by Koken [Japan]) by high-performance liquid chromatography. More particularly, after adsorption of the above-mentioned dialyzed specimen onto the column, elution was carried out with a linear gradient of sodium phosphate of 20 to 400 mM, and fractions containing reverse transcriptase activity were pooled. Thus, purified reverse transcriptase was obtained. The thus obtained reverse transcriptase was confirmed, by the use of SDS-PAGE, to have a purity of over 95%. The yield was 31% relative to the crude extraction liquid.

(EXAMPLE 10)

Diagnosis of HIV-1 infection using purified reverse transcriptase: The purified reverse transcriptase (protein concentration 250 µg/ml) prepared according to Example 9 was electrophoresed on a polyacrylamide gel in accordance with Example 2, and was blotted onto a nitrocellulose membrane. The membrane was then immersed in a 3 W/V% gelatin solution for blocking. Subsequently, the presence of an antibody against the HIV-1 reverse transcriptase was investigated in the sera of human HIV-1 carriers (3 subjects) using the Western blot technique. Human T-cell leukemia virus (HTLV-1) carriers (5 subjects) and healthy adults (5 subjects) were similarly investigated. The result in shown in Table 1. The sera of all 3 HIV-1 carriers reacted to reverse transcriptase (66 kd and 51 kd). However, none of the sera of the HTLV-1 carriers (which belongs to the same retrovirus family as HIV-1), nor the sera from the 5 healthy subjects did so. This suggests that it is possible to make a specific diagnosis of the presence of HIV-1 infection by using the purified HIV-1 reverse transcriptase prepared from *Escherichia coli* according to the present invention.

TABLE 1

Diagnosis of HIV-1 infection by Western blotting, using the purified reverse transcriptase.

| Subjects | Reactivity |
|---|---|
| human serum of HIV-1 carrier | |
| 1 | +** |
| 2 | + |
| 3 | + |
| human serum of HTLV-1 carrier | |
| 1 | − |
| 2 | − |
| 3 | − |
| 4 | − |
| 5 | − |
| human serum of healthy adult | |
| 1 | − |
| 2 | − |
| 3 | − |
| 4 | − |
| 5 | − |

\* Specific immunological reaction against purified reverse transcriptase
\*\* Reactivity was measured by the Western blot technique. Shown are positive (+) and negative (−) reaction.

EFFECT OF THE INVENTION (1) In the method of the present invention, in which a very dangerous retrovirus itself is not used, high safety is available from the point of view of biohazards under the production conditions, and operation is easy.

(2) The method of the present invention provides a very high production yield of each of the enzymes produced as present by an amount of protein of from 1 to 10 mg per liter of bacteria culture.

(3) According to the present invention, in spite of the retroviral protease, reverse transcriptase and integrase are expressed as a fusion protein with high expressing ability, various enzymes can be produced, not in the form of fusion protein, but in the form of single matured proteins which had been processed respectively. The method is thus more efficient and rational than that using the expression of single enzyme genes, and taking account of the effects (1) and (2) above, is more economical.

(4) Since enzymes having a very high specificity relative to the substrate unique to retroviruses and enzymes as antigen to retroviruses are available at a low cost in a large quantity, the method of the present invention brings about great progress in fundamental research on and diagnosis of retrovirus infectious diseases such as AIDS, adult T cell leukemia, avian sarcoma or leukemia, and feline leukemia, and facilitates development of specific therapeutic drugs and preventive drugs having a high selectivity, thus providing a boon to human health and promotion of stock breeding.

(5) The method of the present invention can be applied to development of the efficient and rational mass production of the foregoing gene products, for this method makes it possible to cause mass expression of various other genes contained in the said virus and retrotransposon, as well as of various retrovirus enzyme genes.

What is claimed is:

1. A method for producing retroviral enzymes comprising the steps of:

(a) preparing a cDNA fragment from HIV-1 or RSV pol gene sequences which consists of one or more retroviral genes encoding a retroviral enzyme selected from the group consisting of protease, reverse transcriptase and endonuclease, wherein the retroviral gene or genes are a sequence from the 5'-end to the 3'-end of the cDNA fragment, encoding:

protease;
protease and reverse transcriptase;
reverse transcriptase and protease;
protease and endonuclease; or
protease, reverse transcriptase and endonuclease;

(b) constructing an expression vector by inserting the cDNA fragment into a pUK290 series plasmid DNA series in a matching reading frame with lacZ gene thereof;

(c) introducing the expression vector into a lon-recipient E. coli cell to transform the cells; and (d) culturing the transformed cells under two-stage culturing conditions consisting of a first culturing stage for 1 to 24 hours at 10° to 40° C. prior to induction and a second culturing stage for 1 to 40 hours at 10° to 35° C. following the induction, whereby the retroviral gene or genes are expressed as one or more separate mature enzymes, wherein in the case of an enzyme selected from reverse transcriptase and endonuclease being coexpressed with the protease, the transformed cells are cultured for 3 to 35 hours at 15° to 28° C. under the second culturing stage.

2. The method according to claim 1 wherein the cDNA fragment is selected and prepared from *E. coli* UT481/ PNLH402 (FERM BP-2417) OR *E. coli* JM109/ pSRA2(FERM BP-3921).

* * * * *